United States Patent
Carruthers (10) Patent No.: US 6,645,954 B2
(45) Date of Patent: Nov. 11, 2003

(54) COMPOSITIONS COMPRISING ETHISTERONE OR ITS DERIVATIVES

(75) Inventor: Malcolm Carruthers, London (GB)

(73) Assignee: Multimed Limited, London (GB)

(*) Notice: Subject to any disclaimer, the term of this patent is extended or adjusted under 35 U.S.C. 154(b) by 0 days.

(21) Appl. No.: 10/117,210

(22) Filed: Apr. 8, 2002

(65) Prior Publication Data
US 2002/0115648 A1 Aug. 22, 2002

Related U.S. Application Data

(63) Continuation of application No. 09/647,663, filed as application No. PCT/GB99/00984 on Mar. 29, 1999.

(30) Foreign Application Priority Data

Apr. 9, 1998 (GB) .............................................. 9807809

(51) Int. Cl.[7] .............................................. A61K 31/56
(52) U.S. Cl. ........................ 514/171; 514/177; 514/178
(58) Field of Search ................................. 514/171, 178, 514/177

(56) References Cited

U.S. PATENT DOCUMENTS

| 5,135,849 A | 8/1992 | Soto et al. |
| 5,708,038 A | 1/1998 | Davis |
| 5,855,905 A | 1/1999 | Oettel et al. |

FOREIGN PATENT DOCUMENTS

| EP | 0 804 926 | 11/1997 |
| WO | WO 95/13800 | 5/1995 |
| WO | WO 97/24148 | 7/1997 |

OTHER PUBLICATIONS

Maas et al., Drugs & Aging, 1997; 11(1):45–60.*

Berkow, "Gonads," Merck Manual of Diagnosis and Therapy, Section 90, pp. 1032–1037. 1992.

Dowsett et al., "A Comparison of the Effects of Danazol and Gestrinone on Testosterone Binding to Sex Hormone Binding Globulin in vitro and in vivo," CAPLAS, 1986:454783, Abstract.

Nilsson et al., "Danazol and Gestagen Displacement of Testosterone and Influence on Sex–Hormone–Binding Globulin Capacity," CAPLAS, 1982:520740, Abstract.

DRUGLAUNCH, Abstract No. 95:720. 1995.
DRUGLAUNCH, Abstract No. 94:64276. 1994.
DRUGLAUNCH, Abstract No. 94:19186. 1994.
DRUGLAUNCH, Abstract No. 97:4933. 1997.
DRUGLAUNCH, Abstract No. 97:1277. 1997.
DRUGLAUNCH, Abstract No. 96:1496. 1996.
DRUGLAUNCH, Abstract No. 94:67976. 1994.
DRUGLAUNCH, Abstract No. 94:67975. 1994.

Lu et al., "Antifertility Effect of Testosterone Undecanoate in Combination with Danazol in Male Rats," CAPLAS, 1990:30760, Abstract.

Lohiya et al., "Testis Functions and Sexual Potential in Langur Monkey Treated with a Combination Steroidal Contraceptive Formulation," CAPLAS, 1987:13092, Abstract.

(List continued on next page.)

Primary Examiner—Sreeni Padmanabhan
Assistant Examiner—San-Ming Hui
(74) Attorney, Agent, or Firm—Foley & Lardner (57) ABSTRACT

Treatment of androgen deficiency using a pharmaceutically effective dose of ethisterone or an ethisterone derivative such as Danazol. In particular, androgen deficiency in the aging male, also known as the male climacteric andropause or the male menopause, can be treated by ethisterone or ethisterone derivatives. Treatment of hypogonadism using ethisterone or ethisterone derivative in combination with testosterone is also effective.

6 Claims, 9 Drawing Sheets

OTHER PUBLICATIONS

Lohiya et al., "Changes in the Biochemical Composition of Semen Following Danazol Plus Testosterone Enanthate Administration to the Langur Monkey," CAPLAS, 1985:448346, Abstract.

Reynodls Editor, "Mantindale the Extra Pharmacopoeia," $29^{th}$ Edition, pp. 1395–1396, 1414–1415.

Hammond et al., "Androgen Excess," Danforth's Obstetric and Gynecology, $7^{th}$ Edition, 1994, pp. 681–693. 1989.

* cited by examiner

COMPOSITIONS COMPRISING ETHISTERONE OR ITS DERIVATIVES

This application is a continuation of U.S. application Ser. No. 09/647,663, filed Dec. 15, 2000, which is a 371 of PCT/GB99/00984 filed Mar. 29, 1999 the disclosure of which is incorporated by reference herein in its entirety.

COMPOSITIONS COMPRISING ETHISTERONE OR ITS DERIVATIVES

The present invention relates to the treatment of hypogonadism in men, whether due to an absolute or relative deficiency of testosterone. More specifically, the invention relates to compositions comprising a pharmaceutically effective dose of ethisterone or an ethisterone derivative such as [1,2], oxazolo[4,5-b]17alpha-pregna-2,4-dien-20-yn-17beta-ol; also known as danazol, Danol, Azol (in Australia) and Danocrine (in the USA).

Androgen Deficiency in the Ageing Male, also referred to as 'The Male Climateric', 'The male menopause' and the 'Andropause' causes a highly characteristic pattern of symptoms which was first recognised nearly sixty years ago (Werner, A. JAMA 112, 15, 1441–3, 1939). As described at that time, the syndrome includes loss of energy, drive and libido, depression, irritability, joint pains and stiffness, and even such typical symptoms of the female menopause as night sweats and hot flushes.

It has been found (Carruthers, M. 'The Male Menopause, Harpercollins', London, 1996) that the symptoms associated with this condition arise due to an absolute or relative insufficiency of testosterone, particularly the latter, caused by a reduction in the Free Active Testosterone (FAT); that is a lack of testosterone present in an unbound state in blood plasma. Testosterone in vivo can be bound to sex hormone binding globulin (SHBG) and to a lesser extent, albumin. When bound the testosterone is not freely available to the body or bio-available. One of the best measures of this is the 'Free Androgen Index' (FAI). This is calculated by dividing the Total Testosterone (TT) by the 'sex Hormone Binding Globulin' (SHBG) and multiplying by a hundred to express it as a percentage. In the healthy, asymptomatic male this is normally in the range 70–100%. Symptoms of the andropause regularly appear when this drops below 50%, except in a few cases where the TT is low and the body appears to compensate by reducing SHBG levels to maintain the FAI.

It has been found that hypogonadism and also the male menopause can be prevented or treated by freeing bound testosterone so that it becomes bioavailable again. Testosterone may be freed, for example, by:

1. decreasing the number of potential binding sites available for testosterone in vivo, for example by reducing the level of SHBG using compounds which antagonise the action of androgens in stimulating SHBG synthesis, and/or
2. introducing an agent which competes for the binding sites, thereby displacing bound testosterone which is returned to systemic circulation.

Pharmaceutical, pharmacological and biological compounds that may act effectively include ethisterone and ethisterone derivatives and/or precursors.

One such compound, danazol, is a well established therapeutic agent which has been extensively used in the female for managing a wide range of conditions such as endometriosis, menorrhagia and benign breast conditions such as mastalgia and cystic disorders. Its use in the male is not widely known and has been limited to treatment of enlargement of the male breast (gynaecomastia) and limited research into its use as a male contraceptive. The previous uses of danazol in women and men have all been at relatively high concentrations, for example doses of 200 to 600 mg, and at these concentrations it has been shown that total plasma testosterone is reduced.

It has now been found that using danazol in the male at dose level reduced from that at which it would be conventionally used, for example at a daily dose of not more than 100 mg, re-introduction of testosterone to the systemic circulation in the form of Free Active Testosterone is remarkably effective; that is the FAT is increased leading to a highly effective treatment of the symptoms associated with hypogonadism and with the male menopause.

Danazol is effective, non-hepatotoxic, and does not have intrinsic androgenic, oestrogenic or progestogenic actions. It is an ideal agent for displacing and hence activating testosterone as it has a high affinity for androgen receptors, low affinity for progesterone receptors, and does not interact with oestrogen receptors to any significant extent The importance of only giving low doses of danazol, for example not more than 50–100 mg daily, to men being treated for hypogonadism is because at this low dose, as shown by the clinical studies described later in this application, there is direct suppression of SHBG synthesis by the liver, with a corresponding increase in FAI, apparently without reduction of endogenous total testosterone production.

According to the present invention, danazol is used in the manufacture of a medicament for the treatment of hypogonadism in the male.

The medicament may be for treatment of hypogonadism resulting from any biological or physical cause. In particular, the medicament may be for treatment of any condition where systemic free active testosterone is reduced due to raised levels of SHBG, for example, conditions caused by concurrent/prior treatment with oestrogens, anti-convulsants and/or exposure to xeno-oestrogens.

The medicament may be for treatment of male humans. The medicament may also be a veterinary pharmaceutical preparation for treatment of male animals (such as bulls or rams) where symptoms of hypogonadism are a problem, for example in breeding stock.

Preferably, the danazol is used in the manufacture of a medicament for the treatment of male menopause.

Preferably not more than 100 mg of danazol, [1,2]oxazolo [4, 5-b]-17alpha-pregna-2,4-dien-20-yn-17beta-ol, is used per daily dose in the manufacture of the medicament, preferably the daily dose of [1,2]oxazolo[4,5-b]-17alpha-pregna-2,4-dien-20-yn-17beta-ol is between 25–100 mg. The dose is varied according to body weight, TT and SHBG concentrations.

Danazol may be administered on its own or as an adjunct to other methods of relieving sexual dysfunction problems in men such as libido disorders and impotence, such as applications of alprostadil (Caverject and Medicated Urethral Systems for Erection—MUSE), and drugs which enhance relaxation of the corpora cavernosae in the penis, for example those which increase nitric oxide production such as the oral preparation sildenafil (Viagra).

According to the present invention in a further aspect danazol, together with testosterone is used in the manufacture of a medicament for the treatment of the male menopause.

Preferably the testosterone is synthetic. It will be appreciated that the action of natural and endogenous testosterone is also enhanced when using the medicament.

Preferably not more than 100 mg of [1,2],oxazolo[4,5-b]-17alpha-pregna-2,4-dien-20-yn-17beta-ol is used with testosterone per daily dose in the manufacture of the medicament, preferably the daily dose of [1,2],oxazolo[4,5-b]-17alpha-pregna-2,4-dien-20-yn-17beta-ol is between 25–100 mg. Preferably, the daily dose of testosterone used in the manufacture of the medicament is in the range of 80–240 mg. The doses of [1,2],oxazolo[4,5-b]-17alpha-pregna-2,4-dien-20-yn-17beta-ol and testosterone are varied according to body weight, TT and SHBG concentrations According to a still further aspect of the invention there is provided a pharmaceutically acceptable medicament in a dosage form of 25 mg or 50 mg or 75 mg or 100 mg per day of danazol and excipient.

Preferably the pharmaceutically acceptable medicament also includes testosterone.

According to a still further aspect of the invention there is provided a pharmaceutically acceptable medicament which includes danazol and testosterone.

DETAILED DESCRIPTION OF THE INVENTION

Embodiments of the present invention will now be illustrated with reference to the drawings in which.

[1,2], oxazolo[4,5-b]-17alpha-pregna-2,4-dien-20-yn-17beta-ol, also known as danazol (Danol) is one of a series of heterocyclic steroids distinguished by the presence of an isoxyazole group on the A ring of the parent compound ethisterone (17beta-hydroxy-17-alpha-pregn-4-en-20-yn-3one). When administered danazol may, depending on dosage and dose regime, be metabolized to form the following:

1. Ethisterone (17-hydroxy-17alpha-pregn-4-en-20-yn-3-one)
2. 17-hydroxy-2alpha-(hydroxymethyl)-17alpha-pregn-4-en-20 yn-3-one
3. 17-hyroxy-2-(hydroxymethyl)-17alpha-pregna-1,4-dien-20-yn-3-one
4. 6beta,17-dihydroxy-2alpha-(hydroxymethyl)-17alpha-pregn-4-en-20-yn-3-one
5. 6beta,17-dihydroxy-2alpha-(hydroxymethyl)-17alpha-pregna-1,4-dien-20-yn-3-one.

The dosage level required for the activity is much lower than that used in known dose regimes where danazol is used in the female to treat, for example endometrosis. The preferred dosage is between 25–100 mg per day as opposed to 200 to 800 mg per day used previously in different treatments. The dose may be administered orally, nasally, as a solid implant, or intravenously, intramuscularly or transdermally. The active agent may be administered with a suitable carrier or excipient such as lactose (in the case of an orally administered capsule or pill) or as a suspension in an oil such as mannitol. In the case of admistration by injection a suitable solvent such as saline solution may be used.

In a preferred embodiment a dose of 50 mg of danazol is administered to the patient daily in the form of a capsule.

In another embodiment the danazol is administered daily in combination with a daily dosage of testosterone. The testosterone may be synthetic testosterone. When danazol is administered with testosterone the two may be administered together in a single oral dose, transdermally, by nasal application or by injection or implant, or in two separate doses which may be administered by different dosing methods. For example the combination of methods may comprise an oral dose of danazol in combination with an intramuscular injection of testosterone. In one embodiment a dose of 50 mg of danazol is administered to the patient daily in combination with a daily dose of testosterone in the range of 80–240 mg. In a preferred embodiment a dose of 50 mg of danazol is administered to the patient daily in combination with a daily dose of 160 mg testosterone.

The dose range for testosterone varies with the preparation used and the route of administration. For example, the different dosages of three currently used preparations, testosterone undecanoate (Restandol), mesterolone (Pro-Viron) and implants of pure crystalline testosterone when applied with and without danazol are described in the clinical study.

Whatever the form of testosterone treatment given, and whatever the route of administration, whether orally, by implantation, by intramuscular or subdermal injection, transdermally or even nasally, in many cases, especially those with elevated SHBG levels, the addition of ethisterone or ethisterone derivative will enhance the clinical effectiveness of the testosterone and reduce the amount of it required. For example, many cases of hypogonadism resistant to oral testosterone treatment which would previously have required pellet implantation to get a satisfactory clinical effect, respond to the oral treatment plus danazol, and at a lower testosterone dosage level. Furthermore it prolongs the duration of action of testosterone treatments, extending the 'therapeutic window' for free, active testosterone, and making oral doses twice daily as effective as those given three times a day in isolation. It has also been observed to prolong the period of efficacy of both injected and implanted testosterone preparations. This enables reduced dosage to be given with the same duration of action, or the same dosage with an extended duration of action. Because testosterone preparations tend to be expensive, this also has financial implications in reducing the cost of treatment.

It may be that because of the lower doses of testosterone required, or because of its intrinsic pharmacological effects, danazol can reduce the conversion of testosterone to oestrogens. This effect is most marked when high dosages of testosterone given orally as with testosterone undecanoate (Restandol), intramuscularly as with testosterone enanthate, or by pellet implant.

In the following examples the following abbreviations are used:

ACL—Andropause CheckList Score—A questionnaire rating the incidence and severity of symptoms of the andropause. The greater the checklist score, the more severe are the symptoms.

TT—Total Testosterone in nmol/l (NR 13–35)

SHBG—Sex Hormone Binding Globulin in nmol/l (NR 20–45)

FAI—Free Androgen Index (NR 70–100%)

FSH—Follicle Stimulating Hormone in IU/l (NR 1–6)

LH—Luteinising Hormone in IU/l (NR 0.7–6)

E2—Oestradiol in pmol/l (NR 55–165)

PSA—Total Prostate Specific Antigen in ug/l (NR<4.0)

R2, R3, R4, R6—2, 3, 4 or 640 mg capsules of testosterone undecanoate (Restandol) orally, daily in divided doses.

P2, P3, P4, P6—2, 3, 4 or 625 mg tablets of mesterolone (Pro-viron) orally, daily in divided doses.

TI—6-10×200 mg of testosterone implants given into the gluteal region at 6 monthly intervals.

D0.5, D1—danazol (Danol) 100 mg orally alternate days or daily, respectively.

NR is normal range in a healthy subject.

EXAMPLE 1

A 69 year old man presented complaining of erection problems for 3 years, aches and pains in his hands and feet, and dry skin on his hands, giving an ACL of 8. His TT was normal at 27.4, but his SHBG was raised at 73, giving an FAI of 38%. The diagnosis of hypogonadism was confirmed by raised LH of 6.1 and an FSH of 117.

On this basis, he was started on R3, and at monthly intervals this was increased to R4 and then R6 with only partial relief of symptoms. This was reflected in a lowering of his TT to 21.4, which even with Restandol alone produced reduction of SHBG to 47, gave an FAI of 46, with an LH of 6.7 and FSH of 8.9, and raised E2 of 178.

He was therefore put on TI, and his erection problems rapidly improved. A year later his TT was 35.6, his SHBG had risen to 74, with an FAI of 48%, and total suppression of FSH and LH. However, 3 years after starting treatment his symptoms reappeared, and it was decided to add D0.5 and then D1, which reduced his ACL to 3. Endocrinology after 6 months showed a TT of 21, SHBG 32, FAI 66, LH and FSH<0.5, and E2111. This ACL and endocrine profile, with an SHBG less than half its original level, and normal PSA, biochemistry and haematology has continued for a further 3 years on TI+D1.

EXAMPLE 2

A forty-four year old man presented with fatigue for 4 years, and erection problems and reduced libido for 2 years. These symptoms, together with dry skin, sweating and hot flushes gave an ACL of 25. A right undescended testis had been removed 32 years previously, being the most likely cause for an early onset of hypogonadism. Endocrinology showed a low TT of 9.2, high SHBG of 64, giving an FAI of 14%, with raised FSH and LH.

Because of a poor clinical response to either P4 or R4, he was given I2, which relieved his symptoms, but became infected on several occasions, with extrusion of pellets.

It was therefore decided to revert to oral treatment with P2, which with the addition of D0.5 became fully effective and gave an ACL of 4, with TT of 15.1, SHBG of 20.2 and FAI of 75%. This highly satisfactory clinical situation has been maintained now for 2 years, with normal PSA, biochemistry and haematology.

EXAMPLE 3

A 57 year old man presented with a 3 year history of severe stress followed by fatigue, reduced libido, night sweats, and aches and pains. He had a vasectomy 1 year previously which is a contributory factor to andropause in 20–40% of cases. His ACL was 10, with a TT of 20, SHBG 56.7, FAI 35, FSH 10.2 and E2<20. As he needed R6 to control his symptoms, and after 3 months on this his TT was 22.2 but his SHBG had risen to 112, giving an FAI of 19.8, it was decided to try TI. After 6 months, his TT was 30.6, SHBG remained very high at 95.3, giving an FAI of 32%. During the following 2 years with TI alone, the SHBG's were 82.1, 85, 54, and 81. It was therefor decided to add D0.5 to the 6 monthly implant regime, and the SHBG's fell to 35, 34, and 24. This gave optimal clinical results, with high FAI's and no abnormalities of PSA, biochemistry or haematology.

EXAMPLE 4

The 43 year old patient was complaining of fatigue for 5 years, and reduced libido and erection problems for 2 years, with an ACL of 34. He gave a history of removal of a left sided varicoele, followed by severe scrotal swelling, 7 years ago, and non-specific urethritis which is a common contributory factor to hypogonadism, 22 years ago. His TT was 14, and SHBG 66, giving an FAI of 21%, FSH 6.9, LH 6.6 and E284.

With this diagnosis of hypogonadism, largely due to a raised SHBG, he was started on P4+D0.5 At 3 months, his symptoms were largely relieved, the ACL having been reduced to 9, and his libido and erections had improved with daily or twice daily intercourse and reported stupendous orgasms. The TT was 31, SHBG 27, FAI 115%, FSH 5.1, LH 1.6 and E273.

The patient has remained relatively asymptomatic, with ACL's under 7 for the last two years, SHBG's of 18, 23, 24, and 22, PSA's, full biochemistry and haematology profiles staying normal.

EXAMPLE 5

A 42 year old man complained of fatigue, depression, aches and pains in the hands and feet, hot flushes, a feeling of premature ageing, reduced libido and erection problems for 2 years, giving an ACL of 26. He gave a history of having had mumps 10 years before, and stress from his marriage. Surprisingly his TT was raised at 50, but with an SHBG of 72, giving an FAI of 69.4. The FSH was 5.9, LH 6.0 and E2120.

Because of the characteristic clinical picture of the andropause, it was decided to treat him with D1 alone. Within 3 months his sexual activity had increased from once a month to twice a week, and his ACL had reduced to 14. His testosterone had remained high at 48, the SHBG was down to 39, giving a FAI 123%, with an FSH of 4.5, LH 2.9, and E2<44. The clinical response has been maintained for 2 years with SHBG's of 17, 19 and 23, again with no adverse effects on PSA, the full biochemistry or haematological profile.

EXAMPLE 6

A patient aged 51 presented with lethargy and depression for 4 years, reduced libido for 3 years, night sweats for 1 year, and an ACL of 39. The TT was 17, SHBG 58, FAI 29%, FSH 2.8, LH 2.2, and E2<37.

On R6+D1 at 3 months his symptoms had decreased somewhat, his ACL being 25. His TT was 58, which with an SHBG of 20 gave an FAI of 290%, the FSH being 1.0, LH 0.7 and E2117. This appeared excessive, and so he was changed to R4+D1, and 6 months after starting treatment he had been able to come off antidepressants, and his ACL was 21. Most unusually, on R4, which is an average dose, combined with D1, TT have remained well above the usual levels achieved, at 46, 64 and 50, with corresponding SHBG's of 23, 23 and 20, giving FAI's of 200, 278, and 250 at the 6 monthly follow-up visits. The clinical results of a further reduction of testosterone dosage to the lowest level of R2, following the principle of restoring the endocrinology to as normal a pattern as possible and using the smallest doses of hormones which will achieve this, so far seem to be excellent.

EXAMPLE 7

The 51 year old patient was complaining of reduced libido and depression for 5 years, with night sweats for 3 years and an ACL of 19. The TT was 18, SHBG 52, FAI 35% FSH 5.2, LH 4.6 and E279. After 3 months on R4+D1, his ACL had fallen to 8, sexual activity had doubled, and his TT was 41, SHBG 15, FAI 273%, FSH 1.0, LH<0.5 with an E2 of 62. Reducing to R2+D1, the clinical benefits were fully maintained, the endocrine results 6 months later being TT 19, SHBG 15, FAI 127%, FSH 1.9, LH 0.9, and E240. One year later, they were TT 20, SHBG 20, FAI 100%, FSH2.3, LH 1.2 and E244.

CLINICAL TRIAL

The following is included by way of further exemplification of the use of the medicament according to the invention.

One thousand men aged 31–80 (mean age 54), were seen in a private clinic, the Gold Cross Medical Centre, complaining of a range of symptoms which to them or their GP indicated the "male menopause" or andropause. These consecutive referrals were evaluated at interview by administering a questionnaire, the "Andropause Check List" which rated each symptom on a five point rating scale as being absent (0), slight (1), moderate (2), severe (3) or total (4). It also included questions on the monthly frequency of intercourse and masturbation. A detailed history was taken focussing especially on factors which might affect testicular function and this was entered onto a computerised database (Microsoft Access).

An extensive clinical examination was also carried out, particularly to look for signs of endocrine imbalance such as gynaecomastia or altered hair distribution, as well as alterations in the penis, testes, scrotum and prostate, including scrotal and transrectal ultrasound where necessary.

Fasting blood samples were taken between 9 and 12 am to minimize the effects of diurnal variation, and analyses included the standard full biochemical, lipid and haematology profiles, prostate specific antigen and routine urine analysis. The endocrine assessment included follicle stimulating hormone (FSH) and luteinizing hormone (LH) prolactin, total testosterone (TT), dihydrotestosterone (DHT), sex hormone binding globulin (SHBG), oestradiol (E2) cortisol and either total thyroxine or TSH.

In addition to any medication, patients received advice on general measures such as relaxation, reduction of alcohol intake, weight loss and exercise in accordance with the findings on their lifestyle profiles. They were then treated with either testosterone undecanoate (TU-Restandol) 40–80 mg bd (twice daily) or tds (three times daily), or mesterolone (ME-Pro-Viron) 25–50 mg bd or tds, the dosage being adjusted according to clinical response. Implantation of 6–10 200 mg pellets of fused testosterone crystals (TI-Organon) into alternate buttocks at 6 monthly intervals was used as the method of choice in some cases who found oral treatment either ineffective or inconvenient.

As a supplement to any of the above treatments, over the last four years of the study, Danazol (D-Danol-Sanofi Winthrop) 100 mg alt mane (dose taken alternate mornings), or depending on the response, mane daily (dose taken each morning), was added to the androgen regime, particularly in cases with a raised SHBG, and those who did not respond to any of the testosterone treatments alone.

During treatment, the severity of symptoms and level of sexual activity on the Andropause Check List score was reassessed at three monthly intervals, as well as weight, blood pressure, resting pulse rate, full endocrine, biochemical and haematological profiles, and in some cases ultrasound studies of the prostate and testes. In all cases, subjects were used as their own controls in the comparison of the effects of treatment. All results were stored in a specially designed Microsoft Access database, and stabilised analyes were carried out using the SPSS version 9 programme.

Results

The results of 480 men given TU, 129 given TU+D, 141 given ME, 36 given ME+D, 118 given TI and 10 given TI+D were analysed for up to six 3–6 monthly visits i.e. up to 3 years, visit 1 representing the paired pre-treatment findings for the same individuals in each case i.e. using each man as his own control.

Figure 1:
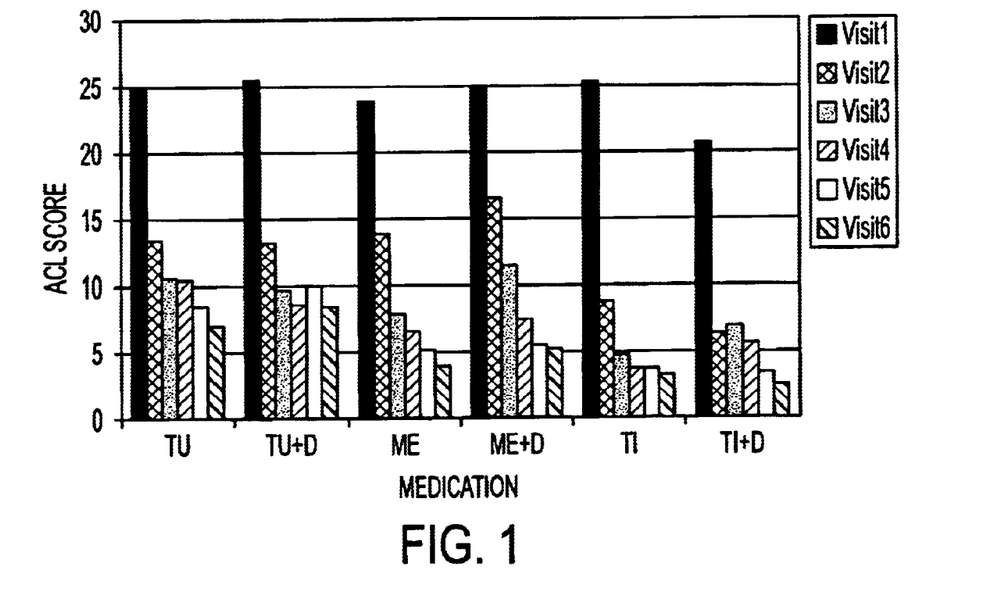
FIG. 1 is a chart showing Andropause Check List scores (ACL) on visits to the clinic (visit 1–6) comparing ACL scores for various subjects under dosage regimes of Restandol (TU), Restandol with Danazol (TU+D), Mesterolone (ME), Mesterolone+Danazol (ME+D), Fused Testosterone Crystals (TI) and Fused Testosterone Crystals+Danazol (TI+D)

The severity of the symptoms as assessed by the total Andropause Check List (ACL) score fell equally in those cases when Danazol (Danol) had to be added, even though many of these cases had previously been resistant to treatment (FIG. 1)

Figure 2:
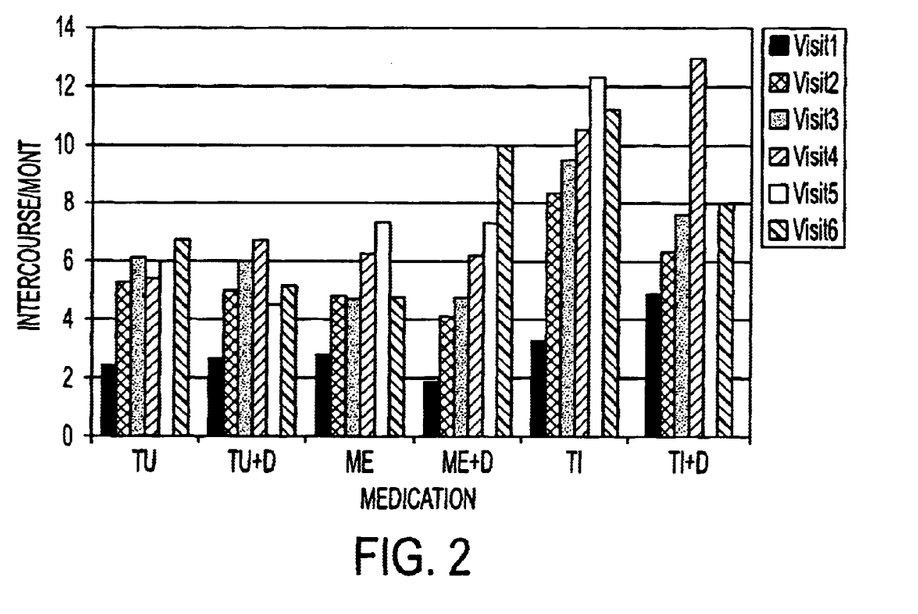
FIG. 2 is a chart showing the total sexual activity per month reported by subjects after each visit to the clinic, for the dosage regimes detailed in the description of FIG. 1.

Sexual activity in terms of intercourse per month increased equally in cases given Danazol (Danol) who had failed to respond to any of the previous treatments (FIG. 2). Activity was highest in the T1 and D groups.

Figure 3:
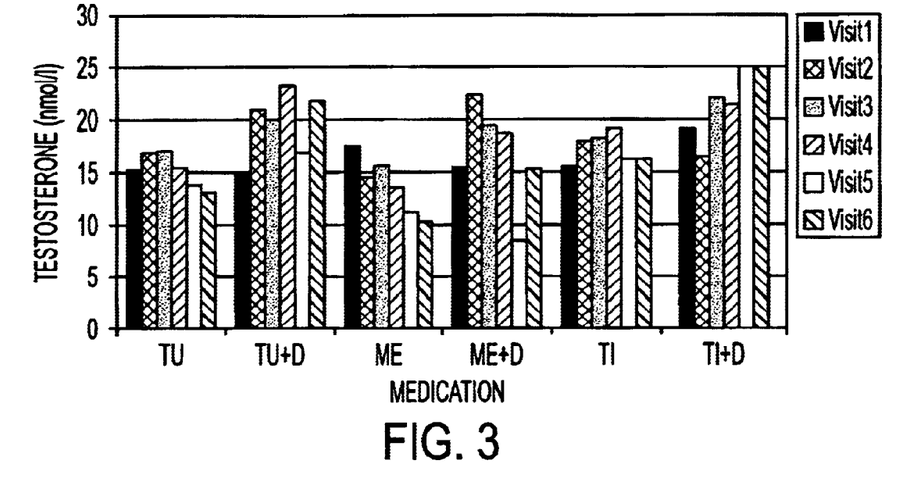
FIG. 3 is a chart showing the concentration of testosterone measured in the subjects at each visit to the clinic, for the dosage regimes described at FIG. 1.

Particularly with Testosterone Undecanoate (TU) and Mesterolone (ME), the addition of Danazol (Danol) appeared to raise the total testosterone levels recorded at the follow-up visits to a statistically significant degree (FIG. 3).

Figure 4:
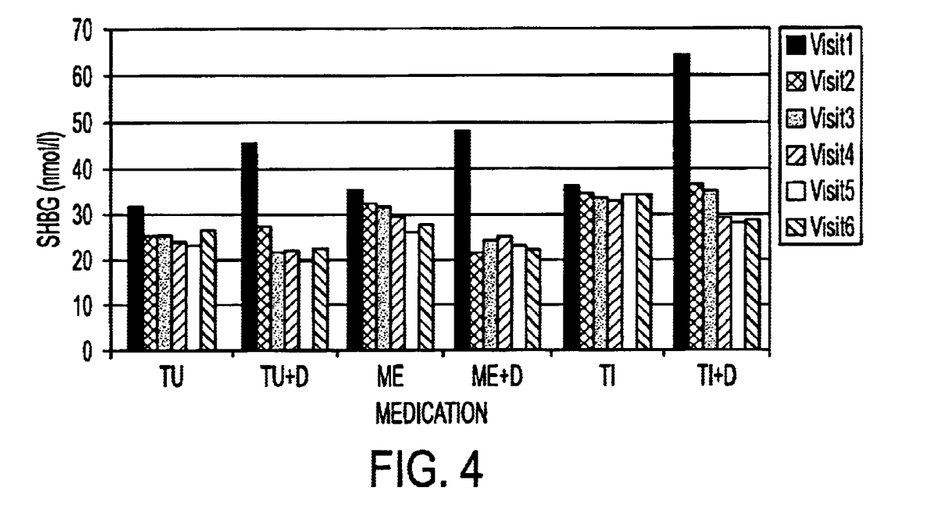
FIG. 4 is a chart showing the concentration of sex hormone binding globulin (SHBG) measured in the subjects at each visit to the clinic, for the dosage regimes described at FIG. 1.

The most marked change observed when Danazol (Danol) was added to the treatment regime was in the reduction of Sex Hormone Binding Globulin, which started above the normal range (20–45 nmol/l) in all three groups where Danazol needed to be given, and uniformly ended at the bottom end of it. Those who required testosterone implants and Danazol (Danol) to obtain a satisfactory clinical response, were observed to have had initially much the highest SHBG levels. Of the three forms of testosterone, only Restandol produced any reduction in SHBG levels on its own (FIG. 4).

Figure 5:
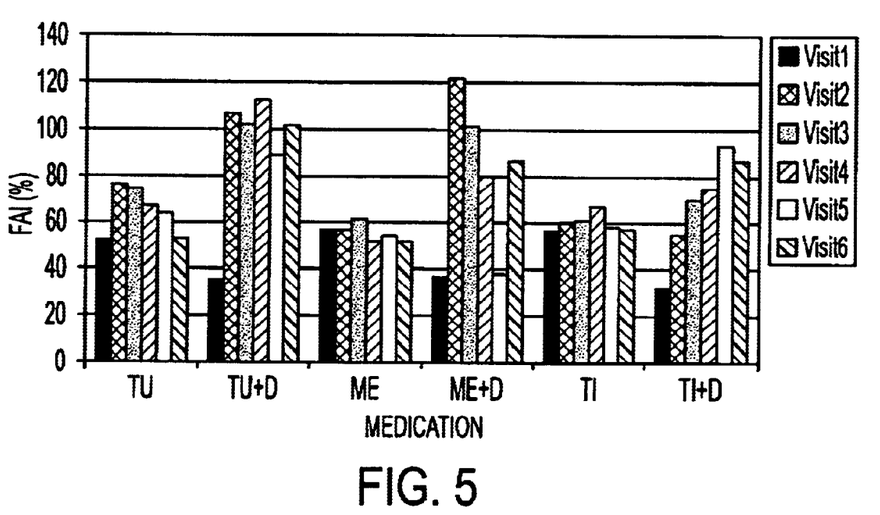
FIG. 5 is a chart showing the percentage free androgen index (FAI) in subjects at each visit to the clinic, for the dosage regimes described at FIG. 1.

The addition of Danazol (Danol) to the three testosterone treatments markedly increased the Free Androgen Indices obtained, in the case of the two oral treatments to nominally in excess of 100% in some cases (FIG. 5).

The effect was almost certainly also present in the implant group, probably to an even greater extent. However it could not be demonstrated in this study because the blood samples were taken at the end of the six month treatment period when the total testosterone levels had fallen back to almost pre-treatment levels as seen in FIG. 3, and symptoms of hypogonadism were beginning to return. In a previous study, samples had been taken 3 months after implantation, and showed mean testosterone levels of 45 nmol/l, which together with the reduced SHBG obtained by Danazol (Danol) treatment would have given an FAI in excess of 100% for most of the six month period.

The pre-treatment FAI's in the groups requiring Danol were lower in all three groups before treatment (Visit 1).

Figure 6:
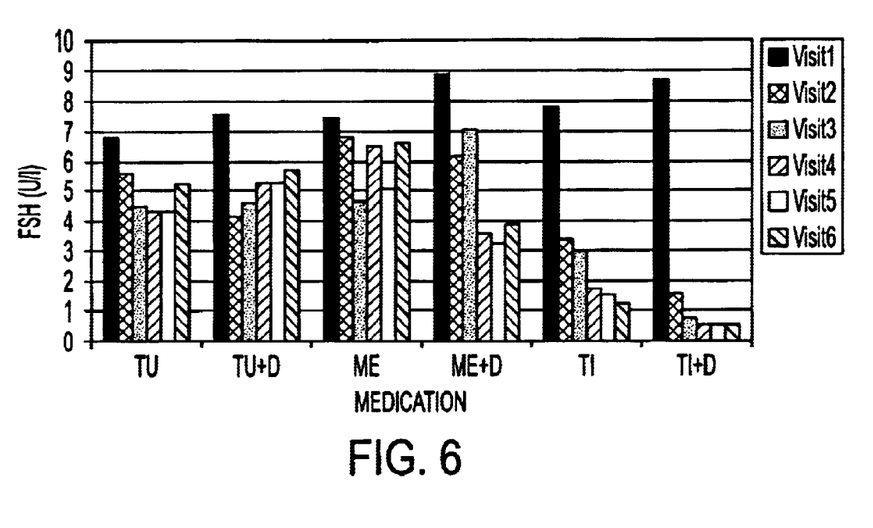
FIG. 6 is a chart showing the concentrations of FSH in the subject at each visit to the clinic, for the dosage regimes described at FIG. 1.
Figure 7:
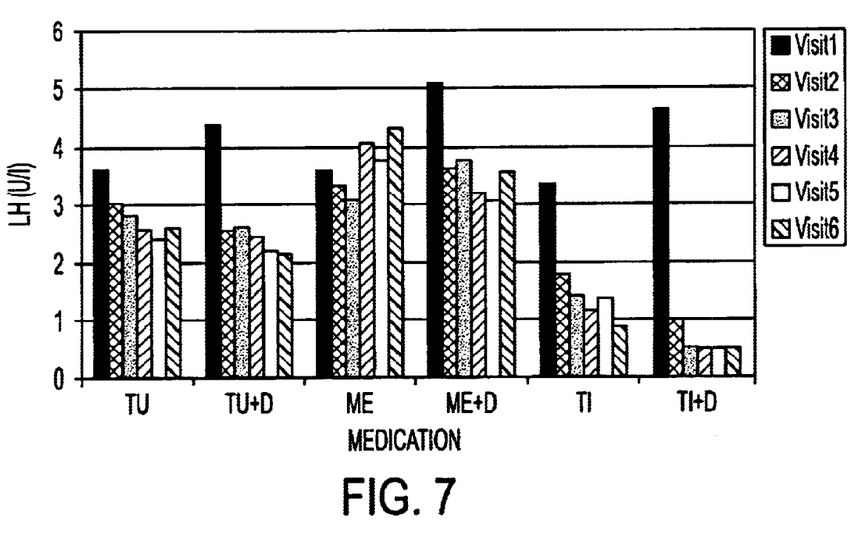
FIG. 7 shows the concentration of luteinizing hormone present in the subjects at each visit to the clinic, for the dosage regimes described at FIG. 1.

Both the gonadotrophins, particularly the FSH, showed greater reductions when Danazol (Danol) was added to the testosterone treatment, probably because of the feedback inhibition of the hypothalamic GnRH due to the much higher FAI's (FIGS. 6 and 7).

Figure 8:
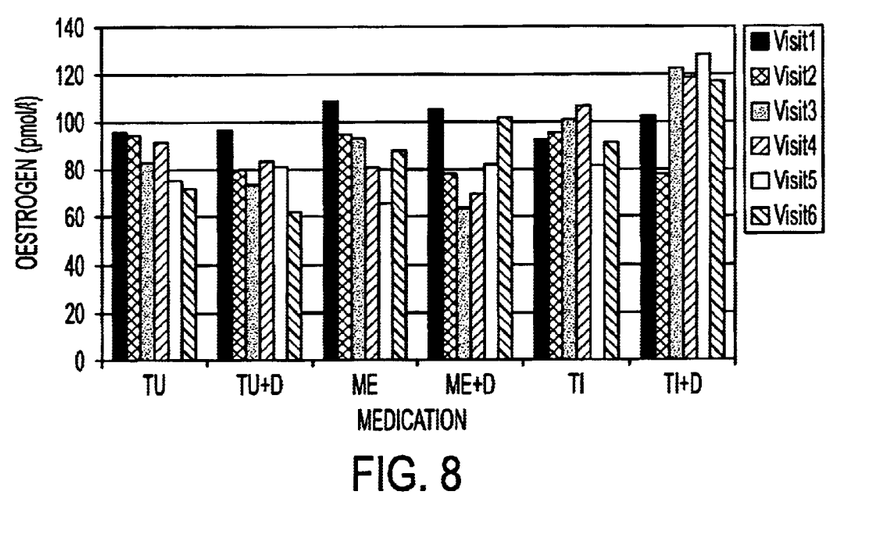
FIG. 8 shows the concentration of oestrogen present in the subjects at each visit to the clinic, for the dosage regimes described at FIG. 1.

There appeared to be no significant change in oestradiol levels with treatment, (FIG. 8) other than possible increase in the TI and D group due to increased aromatisation of the higher total testosterone levels noted previously.

Figure 9:
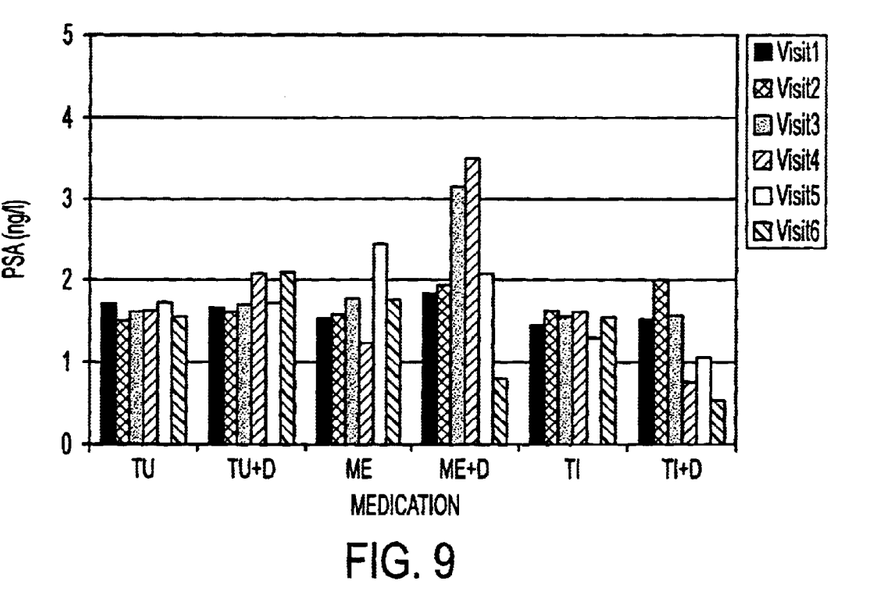
FIG. 9 shows the concentration of prostate specific antigen (PSA) present in the subjects at each visit to the clinic, for the dosage regimes described at FIG. 1.

PSA levels did not appear to change significantly with treatment (FIG. 9), except for a possible increase in the ME+D group, and decrease in the TI+D group This may be related to the trebling of DHT with ME alone, with no increase in the TI alone group. These effects are being investigated further in relation to total and free PSA's and the ratio between them.

The addition of danazol (Danol) to three different forms of testosterone treatment for hypogonadal men greatly increased their efficacy, particularly in cases where SHBG levels were raised. The use of this new agent in the field of treatment of andropausal conditions makes it possible for the first time to specifically reverse the rise in SHBG which tends to occur naturally with age, and restore a more youthful endocrine profile, with the attendant clinical benefits.

Other clinical conditions, such as when there is a rise in SHBG and other carrier proteins due to increased oestrogen levels (Carruthers and Hobbs, J. Clin. Path., 17, 2, 117–9, 1969) as seen in hepatic disease, and with drugs such as anticonvulsants (Toone, B. K. et al. J Neurol., Neurosurg. and psych., 46, 824–6, 1983) and with xanooestrogen's make danazol a valuable preparation either on its own or in conjunction with exogenous testosterone.

The usage of danazol, optionally in combination with low dosage testosterone treatment, appears to give for the first time a unique opportunity to adjust the level of TT, SHBG and hence FAI to mimic a normal youthful endocrine pattern even in middle-aged and elderly men. This should give clinical benefits in both treating hypogonadal men, and in the field of preventive medicine, where maintaining an adequate level of testosterone activity is being shown to be a key factor.

What is claimed is:

1. A method for the treatment of hypogonadism in a male in need thereof, comprising administration of [1,2]-oxazolo[4,5-b]-17alpha-pregna-2,4-dien-20-yn-17beta-ol at a dosage that does not reduce the total testosterone concentration and testosterone.

2. A method according to claim 1, for the treatment of male menopause.

3. A method of treatment of a medical condition caused by elevated levels of Sex Hormone Binding Globulin, comprising administration of [1,2]oxazolo[4,5-b]-17alpha-pregna-2,4-dien-20-yn-17beta-ol at a dosage that does not reduce the total testosterone concentration and testosterone.

4. A method according to claim 1, wherein not more than 100mg of [1,2]oxazolo[4,5]-17alpha-pregna-2,4-dien-20-yn-17betaol per dose are administered.

5. A method according to claim 4, wherein between 25–100 mg of [1,2]oxazolo[4,5]-17alpha-pregna-2,4-dien-20-yn-17beta-ol per dose are administered.

6. A method according to claim 1, wherein each dose includes up to 240 mg testosterone.

* * * * *